United States Patent

Grant

[11] Patent Number: 5,413,120
[45] Date of Patent: May 9, 1995

[54] INTRAVENOUS INJECTION SHIELD ASSEMBLY

[76] Inventor: Michael L. Grant, 6009 Greenview Dr., Oklahoma City, Okla. 73135

[21] Appl. No.: 243,354
[22] Filed: May 16, 1994
[51] Int. Cl.$^6$ ............................................. A61F 5/37
[52] U.S. Cl. ................................... 128/877; 128/878; 128/879
[58] Field of Search ............... 128/846, 877, 878, 879, 128/888; 602/21, 22, 5

[56] References Cited

U.S. PATENT DOCUMENTS

| | | | |
|---|---|---|---|
| 2,443,140 | 6/1948 | Larsen . | |
| 3,722,508 | 3/1973 | Roberts | 128/133 |
| 3,782,377 | 1/1974 | Rychlik | 128/888 |
| 4,505,270 | 3/1985 | Miles | 128/88 |
| 4,517,971 | 5/1985 | Sorbonne | 128/133 |
| 4,870,976 | 10/1989 | Denny | 128/877 |
| 4,919,150 | 4/1990 | Grant | 128/877 |
| 5,018,534 | 5/1991 | Grant | 128/877 |

Primary Examiner—Michael A. Brown
Attorney, Agent, or Firm—Robert K. Rhea

[57] ABSTRACT

An intravenous catheter shield is formed by a base underlying a portion of a hand and forearm of a patient having an inserted infusion needle. The base having side walls interrupted intermediate their ends by a thumb nesting recess. Resilient padding is interposed between the base and the patient's hand and forearm and straps extending transversely across the patient's hand releaseably secure it to the base. An inverted transparent generally U-shaped shield has leg portions removably secured to the inner surface of the base side walls with the bight portion of the shield in vertically spaced relation, with respect to the patient's hand, permitting visual inspection of the catheter at all times.

3 Claims, 2 Drawing Sheets

INTRAVENOUS INJECTION SHIELD ASSEMBLY

BACKGROUND OF THE INVENTION

1. Field of the Invention

This invention relates to medical equipment and more particularly to a guard or shield for catheters.

When intravenous fluid is to be periodically injected into a patient over an extended time period, it has been the general practice to insert a cannula beneath the surface of the skin into a vein and to retain the cannula in position by adhesive tape. This simple arrangement is effective; however, problems can arise in that the adhesive tape sometimes prevent visual inspection of the puncture site and often provides inadequate retention of the cannula as the patient moves or as the nurse inserts a needle to inject other medication.

Further, the adhesive tape is irritating particularly when the patient is sensitive to the adhesive tape which causes irritation and creates considerable discomfort for the patient at the area of the intravenous catheter.

This invention provides a device which immobilizes a patient's hand and provides a transparent shield for the catheter when placed in a vein in the patient's hand.

2. Description of the Prior Art

My U.S. Pat. No. 4,919,150 issued Apr. 24, 1990 and U.S. Pat. No. 5,018,534 issued May 28, 1991 both for INTRAVENOUS CATHETER SHIELD AND RETAINER disclose a planar base underlying a patient's hand and forearm and secured thereto by overlapping Velcro straps extending transversely of the base.

U.S. Pat. No. 4,919,150 discloses a liftoff transparent shield covering the patient's hand and forearm and supporting the catheter tube, while U.S. Pat. No. 5,018,534 similarly discloses a transparent shield overlying the base of patient's hand and forearm and is hingedly connected thereto for permitting access to the catheter.

U.S. Pat. No. 4,505,270 issued Mar. 19, 1985 to Miles for FLUID ADMINISTRATION SPLINT discloses an elongated rigid U-shaped base supporting an animal's leg and includes a cover which overlies a catheter taped to the animal's leg.

This invention is distinctive over these patents by a rigid base having integral forward and rearward upstanding side walls shielding a patient's hand and forearm. Transverse Velcro straps extending over the patients hand and fingers and attached to the base immobilizes his hand. A transparent shield is frictionally maintained in place by resiliently contacting the inner surface of the forward and rearward upstanding walls.

U.S. Pat. No. 3,722,508 issued Mar. 27, 1973 to Roberts for INFUSION GUARD AND IMMOBILIZER discloses a U-shaped channel member underlying a patient's arm and a rigid inverted U-shaped bridge spanning and removably secured to the upstanding edges of the U-shaped channel. The bridge also supports intravenous tubing and the entire unit is secured to the patient's limb by Velcro hook and eye straps.

U.S. Pat. No. 4,517,971 issued May 21, 1985 to Sorbonne for GUARD FOR VENIPUNCTURE SITE AND CATHETER RETAINER discloses a base member taped to a patient limb which supports the intravenous needle or catheter and includes a lid portion hingedly connected at one end to one end portion of the base for movement toward and away from the base, in shielding relation, with respect to the catheter position.

These two last named patents are considered examples of the state-of-the-art.

SUMMARY OF THE INVENTION

An elongated rigid base member dimensioned to underlie a patient's hand and wrist, excluding the thumb, is provided with forward and rearward walls upstanding a distance not greater than one half the width of the base member.

The base is provided with apertures at its juncture with the respective wall through which hook and eye Velcro straps extend transversely of the patient's hand and fingers for securing the base to the patient.

The spacing between the forward and rearward walls forms a recess through which the patient's thumb is extended when lying on the base.

A inverted transversely U-shaped shield formed from transparent resilient material having a memory returning its leg-like walls to their original position after being flexed in a lateral direction is provided with upwardly extending recesses in its respective leg portion coinciding with the position of the base wall recesses for overlying a patient's thumb position and defining a downwardly projecting leg at each forward and rearward side of the shield.

Velcro pads secured to the outer surface of the respective transparent shield leg resiliently contacts a cooperating Velcro pad secured to the inner surface of the respective base wall which maintains the shield in place until manually removed by an attendant. The transparent shield is further provided with a top opening for access to a catheter.

The principal object of this invention is to provide a catheter shield which immobilizes a patient's hand and fingers and permits visual inspection of the catheter at all times and ease in removing the catheter shield when desired.

DESCRIPTION OF THE PREFERRED EMBODIMENTS

Figure 1:
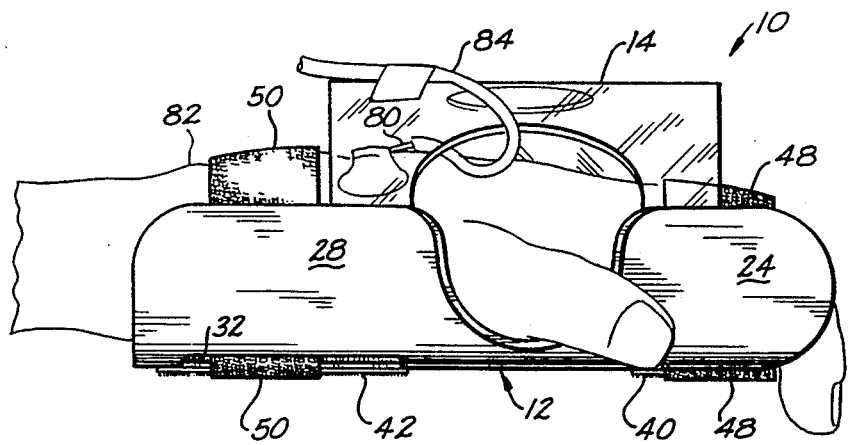
FIG. 1 is a side elevational view of the assembly in operative position on the patient's hand.

Like characters of reference designate like parts in those figures of the drawings in which they occur.

In the drawings:

The reference numeral 10 indicates the device as a whole comprising a base 12 and an overlying transparent shield or cover 14.

The base 12 is formed by a rectangular planar section 16 having forward and rearward parallel ends 18 and 19, respectively. Substantially equal widths of the respective sides of the base 16 are turned upwardly in cooperative upstanding relation and are provided with a U-shaped arcuate surface or recess 20 and 22 in aligned relation transversely of the base 16 to form right or left thumb receiving recesses as presently explained.

Figure 2:
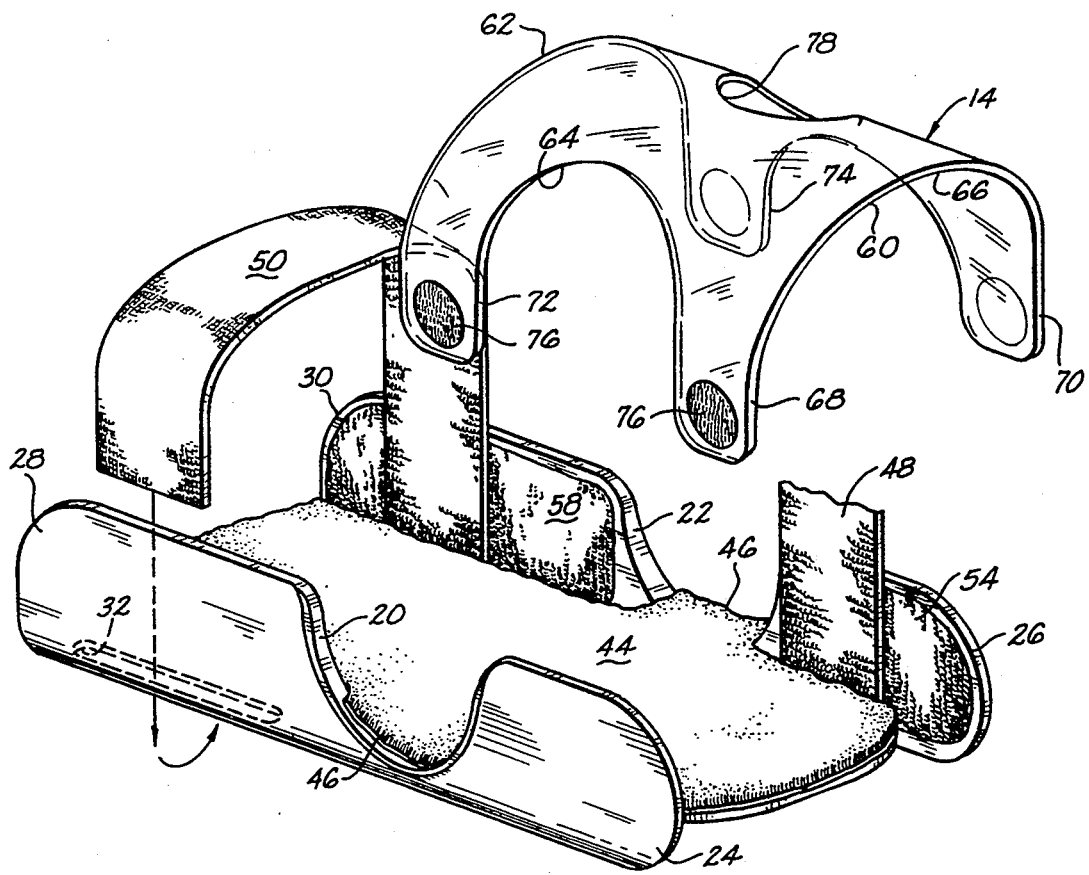
FIG. 2 is a fragmentary partially exploded perspective view of the assembly; and, FIG. 3 is bottom view.

The wall surface forming the respective recesses 20 and 22 is arcuately turned outwardly to form a transversely flat smooth surface for each of the recesses 20 and 22 and act as a stiffener for the side walls. The recesses 20 and 22, thus, define a forward pair of walls 24 and 26 and a rearward pair of walls 28 and 30, as best shown by FIG. 2.

Figure 3:
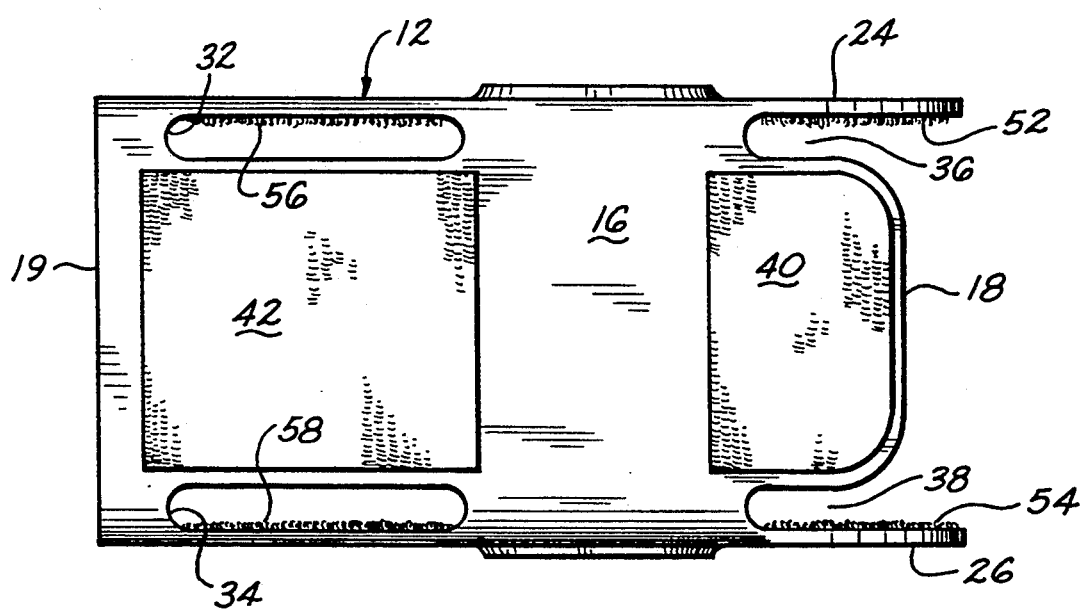

The base 16 is provided with a pair of parallel elongated slots 32 and 34 (FIG. 3) at its juncture with the respective rearward walls 28 and 30 for the purposes presently explained.

Similarly, the forward end of the base 16 is provided with a pair of elongated forwardly open slots 36 and 38 adjacent the juncture of the base 16 with the respective forward walls 24 and 26 to form strap receiving slots.

Rectangular sections of hook and eye fabric fastening material, such as VELCRO, 40 and 42 are bonded to the bottom surface of the base 16 between the respective pairs of slots 36–38 and 32–34 for the purposes presently explained.

Padding or cushioning material, such as a coextensive section of fabric 44, generally referred as sheep skin, contiguously overlies the top surface of the base 16 including laterally projecting sections 46 overlying the bight portion of the respective U-shaped recesses 20 and 22.

Lengths of forward and rearward VELCRO strap material 48 and 50 extend transversely of the base 12 and respective ends of each strap are inserted through the pairs of slots 36–38 and 32–34 and are respectively secured by the bottom VELCRO sections 40 and 42.

Similarly, pairs of Velcro pads 52–54 and 56–58 are secured to the inner surfaces of the forward and rearward pairs of base walls 24–26 and 28–30, respectively, for the purposes presently explained.

The transparent shield 14 is inverted substantially U-shaped in transverse configuration having parallel forward and rearward end surfaces 60 and 62 defining a length for the shield 14 substantially less than the length of the base 12 and having an arcuate bight portion and opposing sides which are centrally recessed in U-shaped fashion, as at 64 and 66, defining transversely aligned pairs of forward legs 68 and 70 and rearward legs 72 and 74.

A generally circular section of VELCRO material 76 is bonded to the outer surface of the respective transparent pairs of legs 68–70 and 72–74 for securing the transparent shield legs to the VELCRO equipped inner surface of the respective base walls.

Additionally, the transparent shield 14 is provided with a top or substantially centrally disposed catheter observing and access opening 78.

Operation

In operation, assuming a catheter 80 has been inserted in the patient's hand, a nurse or attendant places a patient's hand, indicated at 82, palm down on the padding 44 with the patient's thumb projecting outwardly through one of the U-shaped recesses 20 or 22, in accordance with the right or left hand thumb.

The length of the device between these recesses (20 and 22) and the base forward end 18 is such that the end portions of the patient's fingers normally bend downwardly over the forward end 18 of the base for comfort.

The respective ends of the transverse straps 48 and 50 are inserted through the respective cooperating pairs of slots 36–38 and 32–34 and the ends of the straps secured to the base bottom Velcro pads 40 and 42. The forward strap 48 extending transversely of the patient's fingers and the strap 50 extending across the hand rearwardly of the thumb.

The catheter tubing 84 is extended toward one side of the hand 82 and the shield 14 sides are manually squeezed inwardly so that the shield legs 68–70, 72–74 are manually disposed between the base pairs of forward walls 24–26 and rearward walls 28–30, respectively.

The legs of the shield are then manually released and the resilience of the shield material forces the Velcro pads 76 into contact with respective pad on the inner surface of the pairs of forward and rearward walls. The tubing 84 is preferably taped to the exterior surface of the shield. The shield in position over the catheter and the top of the patient's hand permits visual observation thereof.

Obviously the invention is susceptible to changes or alterations without defeating its practicability. Therefore, I do not wish to be confined to the preferred embodiment shown in the drawings and described herein.

I claim:

1. A shield for protecting the position of an intravenous needle inserted into a body part of a patient and having one end of intravenous tubing connected thereto, comprising:

a generally rectangular planar base having top and bottom surfaces and having forward and rearward longitudinally spaced-apart pairs of upright side walls defining a thumb receiving space at respective sides of the base, said base having a longitudinally extending slot adjacent its juncture with the respective side wall of said pairs of side walls;

a layer of self adhesive fabric material bonded to the bottom surface of said base and inner surface of each side wall of said pairs of side walls, respectively;

a plurality of flexible strap means respectively extending through the slots transversely of the base for securing a patient's limb to the base;

an elongated inverted substantially U-shaped transparent shield having forward and rearward pairs of legs depending from its respective end portions and laterally spaced-apart a distance at least equal to the transverse outside dimension between said pairs of side walls, said pairs of legs capable of being manually flexed inwardly toward each other and respectively disposed between said pairs of side walls and returning toward a position of repose against the inner surface of said pairs of base side walls, said shield having an arcuate bight portion longitudinally overlying said base in vertically spaced relation with respect to the surface of a patient's limb when disposed thereon and an intravenous needle location, said bight portion having a top opening whereby a caretaker may finger touch inspect a patient's intravenous needle site; and, a pad of self adhesive fabric material bonded to the outer depending end portion surface of each shield leg of said pairs of legs for removably securing said pairs of legs with said pairs of side walls, respectively.

2. A shield for protecting the position of an intravenous needle inserted into a body part of a patient and having one end of intravenous tubing connected thereto, comprising:

a base having top and bottom surfaces and having forward and rearward pairs of upright side walls defining a thumb receiving space at respective sides of the base, adhesive material bonded to the bottom surface of said base and inner surface of each side wall of said pairs of side walls; flexible strap means extending transversely of the base for securing a patient's limb thereto;

an inverted U-shaped shield having forward and rearward pairs of legs depending from respective end portions and cooperatively received between said pairs of base side walls, said shield having an arcuate bight portion longitudinally overlying said base in vertically spaced relation with respect to a patient's limb supporting an intravenous needle, said bight portion having a top opening whereby a caretaker may finger touch inspect a patient's intravenous needle site; and, self adhesive material bonded to the outer surface of the depending end portion of each shield leg of said pairs of legs for removably securing said pairs of legs to said pairs of side walls, respectively.

3. A shield for protecting the position of an intravenous needle inserted into a body part of a patient and having one end of intravenous tubing connected thereto, comprising:

a base having forward and rearward pairs of upright side walls defining a thumb receiving space at respective sides of the base;

flexible strap means extending transversely of the base for securing a patient's limb thereon;

an inverted U-shaped shield having forward and rearward pairs of legs depending from respective end portions and cooperatively contacting said pairs of base side walls, said shield having an arcuate bight portion overlying said base in vertically spaced relation with respect to a patient's limb supporting an intravenous needle, said bight portion having a top opening for catheter access by a caretaker's finger when touch inspecting a patient's intravenous needle site; and, self adhesive material releasably securing each shield leg of said pairs of shield legs with the respective side wall of said pairs of side walls.

* * * * *